United States Patent [19]

Burns et al.

[11] Patent Number: 5,035,738
[45] Date of Patent: Jul. 30, 1991

[54] AMINOPROPYLMORPHOLINE SALTS, COMPOSITIONS AND USES THEREOF

[75] Inventors: Johnny L. Burns, Chicago, Ill.; Richard Wilson, Corpus Christi, Tex.

[73] Assignee: Sandoz Ltd., Basle, Switzerland

[21] Appl. No.: 289,165

[22] Filed: Dec. 23, 1988

[51] Int. Cl.$^5$ .......................................... C07D 295/13
[52] U.S. Cl. ........................................ 71/88; 544/162
[58] Field of Search ............. 544/162; 71/88, DIG. 1, 71/115; 514/237.8

[56] References Cited

U.S. PATENT DOCUMENTS 3,013,054 12/1961 Richter .................................. 262/474
3,725,031 4/1973 Balassa ................................... 71/115

FOREIGN PATENT DOCUMENTS 161202 5/1985 Fed. Rep. of Germany .
255869 4/1988 Fed. Rep. of Germany .
255870 4/1988 Fed. Rep. of Germany .

*Primary Examiner*—Mary C. Lee
*Assistant Examiner*—Jacqueline Haley
*Attorney, Agent, or Firm*—Gerald D. Sharkin; Richard E. Vila; Joanne M. Giesser

[57] ABSTRACT

Aminopropylmorphine reduces the volatility of biologically active compounds containing a carboxylic acid group, including herbicides, fungicides and insecticides. Preferred herbicidal formulations, include benzoic acid compounds, phenoxy carboxylic acid compounds, glyphosate and mixtures thereof, especially dicamba and 2,4-D.

6 Claims, No Drawings

AMINOPROPYLMORPHOLINE SALTS, COMPOSITIONS AND USES THEREOF

This invention relates to the use of N-aminopropylmorpholine (APM) to reduce the volatility of carboxylic acid bearing biologically active compounds. More particularly, the invention relates to biologically active carboxylic acid-containing compounds in salt form, the same having been found to be of low volatility.

There are numerous carboxylic acid-containing compounds which are pesticides, including those of considerable agricultural importance. These compounds include herbicides, insecticides and fungicides. For numerous reasons, it would be desirable to reduce the volatility of these compounds while not affecting their activity.

It has been found in accordance with the invention that APM is particularly useful in varying amounts in reducing the volatility of biologically active compounds bearing a carboxylic acid group, and may even be used for such purpose upon simple addition to other salt forms.

One aspect of this invention relates to herbicidal compounds, and in particular to N-aminopropylmorpholine (APM) salts of herbicidally active carboxylic acid-bearing compounds. Herbicides which exhibit a low volatility are desirable, since herbicides which are subject to drift may not only be phytotoxic to sensitive off-target vegetation, but may be less effective on target weeds.

It has been found that the N-aminopropylmorpholine (APM) reduces the volatility of carboxylic acid-bearing herbicidal compounds without adversely affecting their herbicidal activity. Thus one aspect of this invention is to provide for the APM salt derivative of such herbicidal compounds and mixtures thereof.

The preferred classes of herbicidal compounds whose volatility is reduced in accordance with this invention are the carboxylic acid-containing compounds which include glyphosate, the benzoic acid compounds, the phenoxy carboxylic acid compounds, and mixtures thereof. Particularly preferred compounds include MCPA (2-methyl-4-chlorophenoxyacetic acid), dicamba (3,6-dichloro-2-methoxy-benzoic acid), and 2,4-D (2,4-dichlorophenoxyacetic acid). A particularly preferred embodiment is a mixture of APM salts of dicamba and 2,4-D. Another herbicidal carboxylic acid of particular interest is glyphosate (phosphono-methyl glycine).

Other biologically active compounds which have carboxylic acid groups and whose volatility is reduced in APM salt form include fungicides and insecticides. Thus another aspect of this invention is a carboxylic acid bearing fungicide or an insecticide in APM salt form. Specific fungicides which may be mentioned for conversion to APM salt form include Curitan ® (N-dodecyl guanidine acetate) and Milban ® (dodemorph acetate).

The APM salt of the biologically active carboxylic acid-containing compound (or mixtures) may be made by combining APM with the biologically active compound either neatly or when the active compound has been previously formulated, including dry or solid formulations as well as liquid formulations such as aqueous formulations. Also, APM may be added to biologically active compounds which are already in another salt form. Such preparations are preferably carried out in aqueous media. For example, APM may be added to dicamba in dimethylamine (DMA) salt form, which is the dicamba salt form currently available from Sandoz Crop Protection Corporation under the trademark BANVEL ®. Generally, the level of volatility reduction is increased as the amount of APM is increased, with minor amounts providing effective results and with greater volatility reduction occurring even with the addition of a stoichemetric excess of APM. This finding is contrasted with conventional salt-forming bases such as dimethylamine (DMA) which do not affect the volatility of the active composition.

Hence, the amount of added APM may vary widely up to the amount required to neutralize the acid or may be in excess of that amount. The amount of APM may be designated with reference to the amount of APM required to bring a simple aqueous solution to a pH of 8. For example, if a composition is "1.5×APM", then it contains 1.5 times the amount of APM necessary to raise the pH to 8. Preferred compositions according to this invention generally contain at least 0.1X APM, and are preferably in the range of 0.1–3× APM, more preferably 0.5–2.5×APM, and most preferably 0.5–1.5×APM.

It has been surprisingly found in accordance with this invention, that when APM is added to a mixture of herbicides, the volatility also decreases in a non-obvious manner. For instance, in one test APM reduces the volatility of dicamba by approximately 65-fold, and similar results are observed for 2,4-D. However, in a mixture of APM salts of both dicamba and 2,4-D, the reduction is over 270-fold. Thus, one aspect of this invention is the APM salt of a mixture of herbicidally active compounds. Preferred mixtures include the APM salts of dicamba and 2,4-D, where the ratio of dicamba to 2,4-D ranges from approximately 1:1 to 1:3.

The invention may also be practiced by combining APM with a biologically active carboxylic acid compound which is already in another salt form, such combination preferably taking place in aqueous media or thereafter mixed in water. In a like manner, APM and a different salt-forming base may be combined with the free carboxylic acid form. In either case, it is indicated that minor amounts of APM are effective to reduce the volatility of the biologically active component in the obtained mixture. Such combination may be used advantageously to reduce the amount of a more expensive APM while maintaining greater total salt formulation and low volatility.

The pesticidally (biologically) active carboxylic acid compounds combined with APM in accord with the invention may be applied and used as pesticides in the same manner and at essentially the same dosages as the parent compounds prior to combination with APM have been used. Somewhat lower dosages may be used in cases where volatility has reduced the actual effectiveness of the parent compound. The invention is of particular interest for use with the compounds having herbicidical activity, such as dicamba, by applying the APM herbicide salt form in a herbicidally effective amount to weed plants.

The invention also includes compositions comprising a biologically active pesticide bearing a carboxylic acid group in APM salt form with or without additional APM in combination with an inert carrier, either in concentrate form or in dilute form for application. Concentrates may be in solid form with conventional inert solid carriers and optionally other conventional adjuvants such as wetting agents, sticking agents and the like. Preferably, the compositions are in liquid form and more preferably comprise water as the inert carrier in an amount at least sufficient to dissolve the APM salt, any other salt or free acid form of the compound present, any excess APM which may have been employed, and optionally adjuvants such as wetting agents and the like. Such compositions may also include other pesticides which do not bear a carboxylic acid group.

The invention may be better illustrated by reference to the following non-limiting examples. Throughout the examples, the term BANVEL® refers to dicamba-DMA.

EXAMPLE 1

The following formulations are used throughout the examples.

| | w/w % |
|---|---|
| I. 2,4-D-DMA 439 g/l or 3.7 lb/gal | |
| 2,4-D Tech (95% ae) | 41.66 |
| DMA (60%) | 14.45 |
| Distilled water | 43.89 |
| | 100.00 |
| II. 2,4-D-APM (1.3 X) 230 g/l or 1.9 lb/gal | |
| 2,4-D Tech (95%) | 21.82 |
| APM | 19.41 |
| Distilled water | 58.77 |
| | 100.00 |
| III. Dicamba-DMA 480 g/l or 4 lbs/gal | |
| Dicamba Tech (80%) | 50.00 |
| DMA (60%) | 17.00 |
| Distilled water | 33.00 |
| | 100.00 |
| IV. Dicamba-APM (0.5 X) 480 g/l or 4 lbs/gal | |
| Dicamba Tech (90.7%) | 43.42 |
| APM | 14.17 |
| Distilled water | 42.41 |
| | 100.00 |
| V. Dicamba-APM (1.5 X) 196 g/l or 1.63 lb/gal | |
| Dicamba Tech (90.7%) | 19.67 |
| APM | 18.64 |
| Distilled water | 61.69 |
| | 100.00 |
| VI. Dicamba + 2,4-D (1:1 ratio) APM (1.4 X) | |
| Dicamba 120 g/l or 1 lb/gal | |
| 2,4-D 120 g/l or 1 lb/gal | |
| Dicamba Tech (88%) | 11.70 |
| 2,4-D Tech (95%) | 10.88 |
| APM | 20.16 |
| Distilled water | 57.29 |
| | 100.00 |
| VII. Dicamba + 2,4-D (1:2 Ratio) APM (1.4 X) | |
| Dicamba 55.2 g/l or 0.46 lb/gal | |
| 2,4-D 110.4 g/l or 0.92 lb/gal | |
| Dicamba Tech (88%) | 5.84 |
| 2,4-D Tech (95%) | 10.85 |
| APM | 15.12 |
| Distilled water | 68.19 |
| | 100.00 |
| VIII. BANVEL® herbicide + APM (0.5 X) | |
| Dicamba 440 g/l or 3.67 lbs/gal | |
| Dicamba (83%) | 42.63 |
| DMA (100%) | 10.61 |
| APM | 11.55 |
| Distilled water | 35.21 |
| | 100.00 |
| IX. BANVEL® herbicide + APM (1.4 X) | |
| Dicamba 333 g/l or 2.8 lb/gal | |
| Dicamba (83%) | 34.63 |
| DMA (100%) | 8.62 |
| APM | 28.16 |
| Distilled water | 28.59 |
| | 100.00 |

EXAMPLE 2

Field Studies of Herbicide Volatility

Herbicide volatility is measured in a common Bermuda grass pasture with plot size of 0.1–1.0 acres. Application of herbicide is made at rates between 1.0–2.0 lbs. active ingredient per acre with a $CO_2$-powered back-pack sprayer and 12 feet boom containing 8 equal-spaced 8004 flat-fan spray nozzles at 28 psi pressure and 26 gallons of water per acre.

Three Gilian model HFO-113A air sample pumps are placed equal distance downwind to the center of the plots, 3 minutes after the completion of the spray application, typically for a period of 8 hours. Air samples are collected at a rate of 2.6 liters per minute into plastic cassettes containing SKC-227-7 filter pads and are analyzed for herbicide levels using standard gas chromatographic procedures and a Hall detector. The limit of detection is 0.01 μg/sample, and results presented are the average of three measurements.

The studies are performed on days when no rain fell. Temperatures range from 75–91° F and relative humidity from 48–74%. Results are presented below.

| Herbicide | Rate (lbs. active ingred. per Acre) | Volatility (μg) |
|---|---|---|
| 2,4-D - DMA | 2.0 | 0.29 |
| 2,4-D - APM | 2.0 | 0.01 |
| dicamba - 1.5 X DMA | 1.0 | 1.13 |
| dicamba - 1.5 X APM | 1.0 | 0.024 |
| BANVEL® | 1.0 | 1.10 |
| BANVEL® + 0.5 X APM | 1.0 | 0.08 |
| BANVEL® + 1.4 X APM | 1.0 | 0.03 |

EXAMPLE 3

Effect of Addition of APM to 2,4-D and Dicamba Mixtures

The following formulations are evaluated using conditions as described in example 2. Results presented below are the averages of three tests.

| Herbicide | Rate* | Volatility (μg) Dicamba | Volatility (μg) 2,4D | Volatility reduction compared to Dicamba-DMA | Volatility reduction compared to 2,4D-DMA |
|---|---|---|---|---|---|
| BANVEL® | 1.0 | 1.1 | — | — | — |
| 1.5 X APM-dicamba | 1.0 | 0.024 | — | 46 X | — |
| 2,4-D (DMA) | 2.0 | — | 0.293 | — | — |

-continued

| Herbicide | Rate* | Volatility (μg) | | Volatility reduction compared to Dicamba-DMA | Volatility reduction compared to 2,4D-DMA |
|---|---|---|---|---|---|
| | | Dicamba | 2,4D | | |
| 1.4 X APM-dicamba + 2,4-D | 1.0 + 1.0 | 0.01 | 0.003 | 110 X | 97 X |
| 1.4 X APM-dicamba + 2,4-D | 1.0 + 2.0 | 0.006 | 0.000 | 183 X | Can't measure |

*lbs. active ingredients per acre based on free acid form.

EXAMPLE 4

Herbicidal Activity in Wheat

The average percent weed control of dicamba salts in wheat is evaluated at various rates of application using 1.0×APM The results presented below represent the average of 6 sites and 14 evaluations. Weeds that are evaluated include:
Amaranthus retroflexus (Pigweed)
Asclepias syriaca (Milkweed)
Brassica campestris (Rape)
Brassica kaber (Charlock)
Cirsium arvense (Canada thistle)
Descurania pinnata (Tansy mustard)
Descurania sophia (Tansy mustard)
Helianthus annuus (Sunflower)
Lactuca serriola (Wild lettuce)
Lamium amplexicaule (Henbit)
Lapsana communis (Nipplewort)
Polygonum convolvulus (Climbing buckwheat)
Rumex crispus (Yellow dock)
Salsola kali (Russian thistle)
Thlaspi arvenge (Field penny-cress)

| Herbicide | Rate of application** (lbs. a.i./acre) | % weed control* |
|---|---|---|
| dicamba-DMA | 0.06 | 74% |
| dicamba-APM | 0.06 | 74% |
| dicamba-DMA | 0.125 | 79% |
| dicamba-APM | 0.125 | 77% |
| dicamba-DMA | 0.25 | 87% |
| dicamba-APM | 0.25 | 86% |

*0% equals no control; 100% equals weed death.
**each formulation includes 0.38 lbs. a.i./acre 2,4-D Thus it is concluded that the APM salt does not impair herbicidal activity.

The amount of injury at various rates of herbicidal application is evaluated in wheat. Results are presented below.

| Salt of dicamba | Rate (lbs. a.i./acre)** | | |
|---|---|---|---|
| | 0.06 | 0.125 | 0.25 |
| | (% wheat injury) | | |
| DMA | 2 | 4 | 12 |
| APM | 3 | 6 | 8 |

**each formulation includes 0.38 lbs. a.i./acre 2,4-D.

Thus it is concluded that the APM salt does not affect injury rate.

EXAMPLE 5

Herbicidal Activity in Corn

The average percent weed control of dicamba salts in corn is evaluated at various rates of applicaiton using 1.0× APM. The results presented below represent the average of six sites. Weeds that are evaluated include:
Abutilon theophrasti (Velvet-leaf)
Amaranthus retroflexus (Pigweed)
Chenopodium album (Lamb's-quarters)
Eleusine indica (Goose grass)
Polygonum pensylvanicum (Pennsylvania smartweed)
Solanum elaeagnifolium (Silverleaf nightshade)
Xanthium pensylvanicum (Common cocklebur)

| Herbicide | Rate of application (lbs. a.i./acre) | % weed control* |
|---|---|---|
| dicamba-DMA | 0.13 | 74% |
| dicamba-APM | 0.13 | 80% |
| dicamba-DMA | 0.25 | 74% |
| dicamba-APM | 0.25 | 78% |
| dicamba-DMA | 0.50 | 85% |
| dicamba-APM | 0.50 | 83% |

*0% equals no control; 100% equals weed death.

The amount of injury at various rates of application is evaluated. Results are set forth below.

| Salt of dicamba | Rate (lbs. a.i./acre) | | |
|---|---|---|---|
| | 0.13 | 0.25 | 0.5 |
| | (% Corn injury) | | |
| DMA | 1 | 4 | 10 |
| APM | 2 | 4 | 9 |

Thus, it is concluded that APM does not affect the herbicidal activity or injury rate.

EXAMPLE 6

Herbicidal Activity in Sorghum

The average percent weed control of dicamba salts in sorghum is evaluated at various rates of application at 1× APM. The results presented below represent the average of four sites. Weeds that are evaluated include:
Amaranthus retroflexus (Redroot pigweed)
Ipomoea lacunosa (Pitted morningglory)
Polygonum pensylvanicum (Pennsylvania smartweed)

| Herbicide | Rate of application (lbs. a.i./acre) | % weed control* |
|---|---|---|
| Dicamba-DMA | 0.14 | 47% |
| Dicamba-APM | 0.14 | 62% |
| Dicamba-DMA | 0.25 | 66% |
| Dicamba-APM | 0.25 | 64% |

-continued

| Herbicide | Rate of application (lbs. a.i./acre) | % weed control* |
|---|---|---|
| Dicamba-DMA | 0.5 | 81% |
| Dicamba-APM | 0.5 | 80% |

*0% equals no control; 100% equals weed death.

The amount of injury at various rates of application is evaluated. Results are set forth below:

| Salt of dicamba | Rate (lbs. a.i./acre) | | |
|---|---|---|---|
| | 0.13 | 0.25 | 0.5 |
| | % sorghum injury | | |
| DMA | 0 | 4 | 13 |
| APM | 1 | 7 | 13 |

Thus, it is concluded that the APM salt does not affect either the herbicidal activity or injury rate.

What is claimed is:

1. A compound which is an N-aminopropylmorpholine salt (APM) of a herbicidally active compound selected from the group consisting of:
   glyphosate,
   2-methyl-4-chlorophenoxyacetic acid (MCPA),
   3,6-dichloro-2-methoxy-benzoic acid (dicamba), and
   2,4-dichlorophenoxyacetic acid (2,4-D).

2. A compound according to claim 1 which is selected from the group consisting of dicamba and 2,4-D.

3. A herbicidally active composition comprising an inert carrier and a herbicidally effective amount of compound of claim 2.

4. A composition according to claim 3 in which the carrier is water in an amount at least sufficient to dissolve the compound.

5. A composition according to claim 3 wherein the composition further comprises APM in an amount equal to or in excess of the amount required to render the pH 8.0.

6. A composition according to claim 3 wherein the APM is present in a total amount of from 0.1× to 3× APM.

* * * * *